United States Patent [19]

Sato

[11] Patent Number: 4,837,339
[45] Date of Patent: Jun. 6, 1989

[54] 4-SUBSTITUTED-1,2,3,6-TETRAHYDROPHTHALIC ACID ANHYDRIDE

[75] Inventor: Fumie Sato, Fujisawa, Japan

[73] Assignee: Nissan Chemical Industries, Ltd., Tokyo, Japan

[21] Appl. No.: 39,726

[22] Filed: Apr. 20, 1987

Related U.S. Application Data

[63] Continuation-in-part of Ser. No. 780,006, Sep. 25, 1985, abandoned.

[30] Foreign Application Priority Data

Sep. 25, 1984 [JP] Japan .................. 59-199855

[51] Int. Cl.$^4$ .............................................. C07F 7/18
[52] U.S. Cl. ..................................... 549/214; 524/112
[58] Field of Search ......................................... 549/214

[56] References Cited

U.S. PATENT DOCUMENTS 3,288,754 11/1966 Green ..................... 260/47
4,381,396 4/1983 Ryang ..................... 549/214

FOREIGN PATENT DOCUMENTS 1114491 10/1961 Fed. Rep. of Germany .
3301807 7/1984 Fed. Rep. of Germany ...... 549/214

OTHER PUBLICATIONS

Douglas C. Batt et al., Tetrahedron Letters, No. 36 (1978), pp. 3323-3324.
F. Sato et al., Chemistry and Industry, (Oct. 15, 1984), pp. 743-744.
A. D. Petrov et al., CA 53:6995h.
Moshinskii et al., CA 71:82053x, 72:32777m.
I. Shologon et al., CA 83:43427a.

Primary Examiner—Robert T. Bond
Assistant Examiner—A. A. Owens
Attorney, Agent, or Firm—Birch, Stewart, Kolasch & Birch

[57] ABSTRACT

A novel 4-substituted-1,2,3,6-tetrahydrophthalic acid anhydride represented by the structural formula [I]:

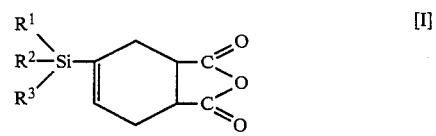

where $R^1$ represents a lower alkoxy group, and $R^2$ and $R^3$ each represents a lower alkyl group or a lower alkoxy group, said 4-substituted-1,2,3,6-tetrahydrophthalic acid anhydride being liquid. The novel compound is useful as coupling agents, plasticizers, curing agents, etc.

8 Claims, No Drawings

4-SUBSTITUTED-1,2,3,6-TETRAHYDROPHTHALIC ACID ANHYDRIDE

This application is continuation-in-part of copending application Ser. No. 780,006 filed on Sept. 25, 1985 now abandoned.

BACKGROUND OF THE INVENTION

1. Field of the Invention

This invention concerns a novel 4-substituted-1,2,3,6-tetrahydrophthalic acid anhydride represented by the structural formula [I]:

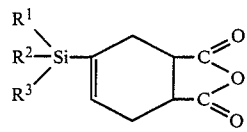

where $R^1$ represents a lower alkoxy group, and $R^2$ and $R^3$ each represents a lower alkyl group or a lower alkoxy group, said 4-substituted-1,2,3,6-tetrahydrophthalic acid anhydride being liquid.

2. Description of the Prior Art

Heretofore, 2-(triethyl)-silyl-1,3-butadiene is described in Tetrahedron Letters as a derivative of an organic silicon compound having a butadienyl group, and preparation of 4-(triethyl)-siyl-1,2,3,6-tetrahydrophthalic acid anhydride therefrom through the reaction with maleic acid anhydride is also described (Tetrahedron Letters, 36, 3323, 1978).

As to such organic silicon compounds the present inventor has found that novel silicon compounds having the butadiene group, that is, 2-substituted-1,3-butadiene compounds, for example, 2-(trimethoxy)silyl-1,3-butadiene, 2-(methoxydimethyl)- silyl-1,3-butadiene, and 2-(dimethoxymethyl)silyl-1,3- butadiene are effective as plasticizers for vinyl chloride resins or the like, silane coupling agents, etc. and have already proposed such novel compounds and the process for producing them (refer to Japanese Patent Application No. 33733/1984 or U.S. patent application Ser. No. 704088).

SUMMARY OF THE INVENTION

As a result of further study on organic silicon compounds derived from the 2-substituted-1,3-butadiene compounds as described above, the present inventor has found that a novel liquid 4-substituted-1,2,3,6-tetrahydrophthalic acid anhydride having both functional group of silyl groups and acid anhydride groups in the molecule represented by the following structural formula [I]:

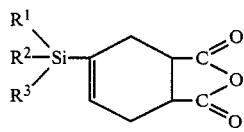

where $R^1$ represents a lower alkoxy group, and $R^2$ and $R^3$ each represents a lower alkyl group or a lower alkoxy group, can be obtained through the reaction between the 2-substituted-1,3-butadiene as described above and maleic acid anhydride, the present inventor has also found that the aforementioned novel liquid compounds can be used effectively as silane coupling agents, particularly coupling agents for polyimide resins, plasticizers for vinyl chloride resins or the like and curing agents for epoxy resins. This invention is based on the above findings.

Therefore, it is an object of the present invention to provide a novel liquid 4-substituted-1,2,3,6-tetrahydrophthalic acid anhydride having the following structural formula [I] which is useful as silane coupling agents, plasticizers, curing agents, etc.

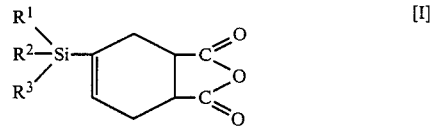

where $R^1$ [I]represents a lower alkoxy group, and $R^2$ and $R^3$ each represents a lower alkyl group or a lower alkoxy group. The novel liquid 4-substituted-1,2,3,6-tetrahydrophthalic acid anhydride of the above-mentioned structural formula [I] is produced by reacting a 2-substituted-1,3-butadiene represented by the structural formula [II]:

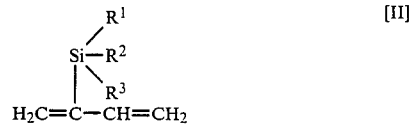

where $R^1$, $R^2$, $R^3$ have the same meanings as described above, with maleic acid anhydride.

Among the 4-substituted-1,2,3,6-tetrahydrophthalic acid anhydrides, a 4-(triloweralkoxy)silyl-1,2,3,6-tetrahydrophthalic acid anhydride where $R^1$, $R^2$, and $R^3$ in the above-mentioned structural formula [I] are lower alkoxy groups and which is represented by the following structural formula [I-a]:

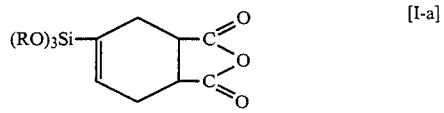

where R represents a lower alkyl group. This compound [I-1] is produced by reacting 2-(triloweralkoxy)silyl-1,3-butadiene, wherein $R^1$, $R^2$, $R^3$ in the structural formula [II] as described above are lower alkoxy groups and represented by the following structural formula [II-a]:

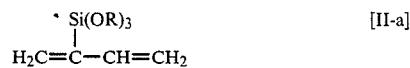

where R represents a lower alkyl groups, with maleic acid anhydride.

Further, a liquid 4-(diloweralkoxy loweralkyl)-silyl-1,2,3,6-tetrahydrophthalic acid anhydride where $R^1$ and $R^2$ are lower alkoxy groups and $R^3$ is a lower alkyl gropu in the above-mentioned structural formula [I] which is represented by the following structural formula [I-b]:

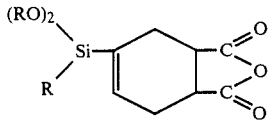

where R represents a lower alkyl group. This compound [I-b] is produced by reacting 2-(diloweralkoxy loweralkyl)silyl-1,3,-butadiene, wherein $R^1$ and $R^2$ are lower alkoxy groups and $R^3$ is a lower alkyl group in the structural formula [II] as described above and represented by the following structural formula [II-b]:

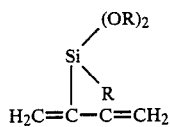

where R represents a lower alkyl group, with maleic acid anhydride.

Furthermore, a liquid 4-(loweralkoxydiloweralkyl)-sylyl-1,2,3,6-tetrahydrophthalic acid anhydride where $R^1$ is a lower alkyl groups in the above-mentioned structural formula [I] which is represented [I-c]

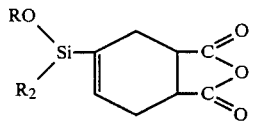

where R represents a lower alkyl group.

This compound [I-c] is produced by reacting 2-(loweralkoxydiloweralkyl)silyl-1,3-butadiene, wherein $R^1$ is a lower alkoxy group and $R^2$ and $R^3$ are lower alkyl groups in the structural formula [II] as described above and represented by the following structural formula [II-c]:

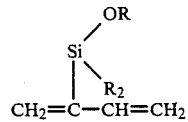

where R represents a lower alkyl group, with maleic acid anhydride.

The novel 4-substituted-1,2,3,6-tetrahydrophthalic acid anhydride is effectively used as a starting material for silicone-containing polyester resins, polyamide resins and addition type polyimide resins; silane coupling agents, particularly, coupling agents for polyimide resins; plasticizers for vinyl chloride resins or the like, curing agents for epoxy resins and the like.

Since the novel 4-substituted-1,2,3,6-tetrahydrophthalic acid anhydride is liquid, the use of the novel compound gives the following merits as compared with the use of solid compound:

(a) mixing with glass cloths, monomers resins or other material is easy,
(b) controlling reaction temperature with glass cloths, monomers, resins or other material is easy, and
(c) handling property is good.

Moreover, since the novel 4-substituted-1,2,3,6-tetrahydrophthalic acid anhidride is liquid, the reaction proceeds easily without any solvents under a mild reaction condition of less than 50° C. to synthesize the compounds of this invention having high purity with little by-products.

The above and other objects, features and advantages of the invention will be more apparent from the following description.

DETAILED DESCRIPTION OF THE INVENTION

The novel liquid 4-substituted-1,2,3,6-tetrahydrophthalic acid anhydride according to this invention, is represented by the above-mentioned structural formula I and it can specifically include, for example; 4-(dimethoxymethyl)silyl-1,2,3,6-tetrahydrophthalic acid anhydride, 4-(trimethoxy)silyl-1,2,3,6-tetrahydrophthalic acid anhydride, 4-(triethyoxy)silyl-1,2,3,6-tetrahydrophthalic acid anhydride, 4-(tripropoxy)silyl-1,2,3,6-tetrahydrophthalic acid anhydride, 4-(tributoxy)silyl-1,2,3,6-tetrahydrophthalic acid anhydride, 4-(dimethoxybutyl)silyl-1,2,3,6-tetrahydrophthalic acid anhydride, 4-(dibutoxyethyl)silyl-1,2,3,6-tetrahydrophthalic acid anhydride, 4-(methoxydimethyl)silyl-1,2,3,6-tetrahydrophthalic acid anhydride and 4-(ethoxydibutyl)-silyl-1,2,3,6-tetrahydrophthalic acid anhydride.

The compound of this invention, 4-substituted-1,2,3,6-tetrahydrophthalic acid anhydride [I] can be synthesized as shown by the following formula (A) through the Diels-Alder reaction between a 2-substituted-1,3-butadiene represented by the structural formula [II] and maleic acid anhydride [III]:

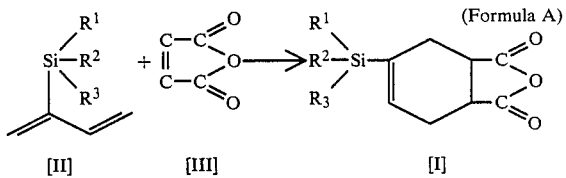

While the Diels-Alder reaction represented by the formula (A) can proceed sufficiently with no solvent, chloroform, benzene, toluene, xylene, cyclohexane, ethyl ether, dioxane, tetralin, tetrahydrofuran or like other solvent may be used if desired. Further, while the reaction is usually carried out at an ambient temperature it may optionally be reacted at the refluxing temperature of the solvent employed. Furthermore, the reaction time may range from about 30 minutes to 10 hours and a catalyst, such as tin chloride and boron trifluoride may be used in the reaction.

In the reaction of the Formula A, the starting material 2-substituted-1,3-butadiene [II] can be prepared by using the compound: 1,4-dichloro-2-substituted-2-butene obtained by the process as shown in the Formula (B), that being, the reaction between 1,4-dichloro-2-butyne and a silane compound.

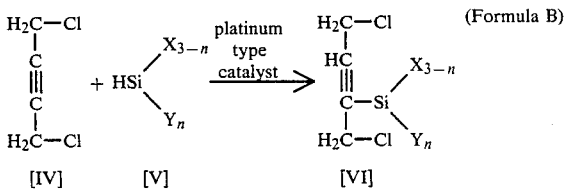

(where X represents a halogen atom, Y represents a lower alkyl group and n is 0 to 2).

For instance, 2-trichlorosilyl-1,3-butadiene [II-d] and 2-triloweralkoxy silyl-1,3-butadiene [II-a] can be synthesized by reacting 1,4-dichloro-2-butyne [IV] and trichlorosilane [V] in the presence of a platinum type catalyst to obtain 1,4-dichloro-2-(trichloro)silyl-2-butene [VI] is then reacted with Zn in a tetrahydrofuran solvent to prepare 2-(trichloro)silyl-1,3-butadiene [II-d], and further reacting the 2-(trichloro)silyl-1,3-butadiene II-d with a lower alcohol in the presence of a base, such as triethylamine, as shown by the following Formula (C):

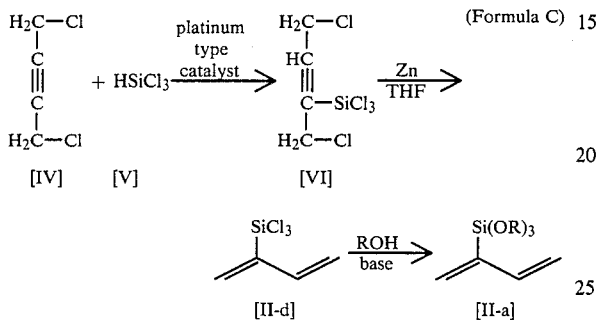

In Formula (C), R represents a lower alkyl group.

Further, 2-(triloweralkoxy)-1,3-butadiene [II-a] can also be prepared by reacting 1,4-dichloro-2-(trichloro)-silyl-2-butene [VI] with lower alcohol in the presence of triethylamine in a tetrahydrofuran solvent to form 1,4-dichloro-2-(triloweralkoxy)silyl-2-butene [VII], and treating the formed 1,4-dichloro-2-(triloweralkoxy)silyl-2-butene [VII], and treating the formed 1,4-cichloro-2-(triloweralkoxy)silyl-2-butene [VII] with Zn in a tretrahydrofuran solvent as shown by the following Formula D:

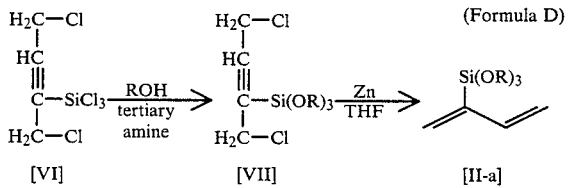

In Formula (D), R represents a lower alkyl group.

Furthermore, 2-(triloweralkoxy)-1,3-butadiene [II-a] can also be prepared by reacting 1,4-dichloro-2-butene [VI] with a triloweralkoxy silane in the presence of a platinum type catalyst to form 1,4-dichloro-2-(triloweralkoxy)silyl-2-butene [VII] directly and then treating the thus formed butene derivative with Zn in a lower alcohol solvent as shown by the following Formula (E):

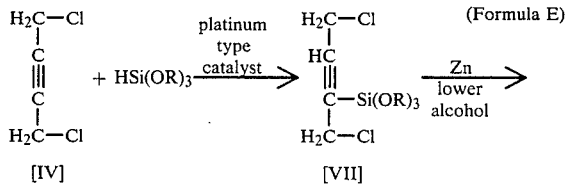

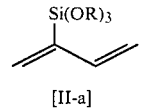

In Formula (E), R represents a lower alkyl group.

In addition, the other starting material 2-substituted-1,3-butadiene, 2-(diloweralkoxy loweralkyl)-silyl-1,3-butadiene may be synthesized in the same manner as in the Formula (D), that being by using 1,4-dichloro-2-(dichloroloweralkyl)silyl-2-butene and 2-substututed-1,3-butadiene, 2-(loweralkoxydiloweralkyl)-silyl-1,3,-butadiene may be synthesized in the same manner as in the Formula (D), that being by using 1,4-dichloro-2-(chlorodiloweralkyl)silyl-2-butene.

The novel material according to this invention is a liquid 4-substituted-1,2,3,6-tetrahydrohthalic acid anhydride represented by the following Formula [I]:

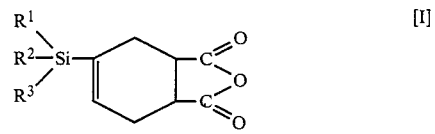

where $R^1$ represents a lower alkoxy group, and $R^2$ and $R^3$ each represents a lower alkyl group or a lower alkoxy group, having functional groups of silyl groups and acid anhydride groups in the molecule as described above. The novel material can be synthesized at a high yield through the reaction between a 2-substituted-1,3-butadiene and maleic acid anhydride and can be used as a starting material for the preparation of silicon-containing polyester resins, polyamide resins and addition type polyamide resins; a silane coupling agent, particularly a coupling agent for polyimide resins; a plasticizer for vinyl chloride resins or the like, and a curing agent for epoxy resins and the like. Among the 4-substituted-1,2,3,6-tetrahydrophthalic acid anhydrides as described above, 4-(triloweralkoxy)silyl-1,2,3,6-tetrahydrophthalic acid anhydride having the above-mentioned structural formula [I-a] and 4-(diloweralkoxy loweralkyl)silyl-1,2,3,6-tetrahydrophthalic acid anhydride having the above-mentioned structural formula [I-b] and 4-(loweralkoxy diloweralkyl)silyl-1,2,3,6-tetrahydrophthalic acid anhydride having the above-mentioned structural formula I-c are particularly suitable for the above-mentioned uses.

This invention will now be described more specifically in the following examples, but it should be noted that this invention is in no way restricted only to there examples.

EXAMPLE 1

To 0.36 g (2.1 mmol) of 2-(trimethoxy)silyl-1,3-butadiene [II], were added 0.19 g (1.9 mmol) of maleic acid anhydride [III] at room temperature and stirred for one hour. After the reaction was over, the reaction product was separated on chromatography using silica gel and developing with a mixed solvent of n-hexane-diethyl ether to obtain 0.44 g of 4-(trimethoxy)silyl-1,2,3,6-tetrahydrophthalic acid anhydride [I] (yield: 80 %, liquid).

HNMR (CCl$_4$): (Internal standard: tetramethylsilane) δ2.05–2.80 (m, 4H, 2CH$_2$), 3.28–3.43 (m, 2H, 2CH), 3.26 (s, 9H, 3CH$_3$OSi), 6.43–6.53 (m, 1H, CH=C)

EXAMPLE 2

64.2 g (0.65 mol) of maleic acid anhydride were dissolved into 65 g of benzene at 45° C., to which were added dropwise 120 g (0.69 mol) of 2-(trimethoxy)silyl-1,3-butadiene [II]slowly while maintaining the reaction temperature at 40°-45° C. After the dropping was completed, stirring was continued for further one hour.

Then, benzene and unreacted 2-(trimethoxy)silyl-1,3-butadiene were distilled off under a reduced pressure. After removing insoluble matters formed slightly through filtration, the filtrate was fractionated to obtain 167 g of clear colorless liquid 4-(trimethoxy)silyl-1,2,3,6-tetrahydrophthalic acid anhydride [I](yield: 94 %).

EXAMPLE 3

64.2 g (0.65 mol) of maleic acid anhydride were dissolved into 65 g of tetrahydrofuran at 45° C., to which were added dropwise 120 g (0.69 mol) of 2-(trimethoxy)-silyl-1,3-butadiene [II]slowly while maintaining the reaction temperature at 40°-45° C. After the dropping was completed, stirring was continued for further one hour.

Then, tetrahydrofuran and unreacted 2-(trimethoxy)-silyl-1,3-butadiene were distilled off under a reduced pressure. After removing insoluble matters formed slightly through filtration, the filtrate was fractionated to obtain 160 g of clear colorless liquid 4-(trimethyoxy)-silyl-1,2,3,6-tetrahydrophthalic acid anhydride [I](yield: 90 %).

A method of synthesizing 2-(trimethoxy)-silyl-1,3-butadiene [II-a]is shown as a reference example.

EXAMPLE 4

212.0 g (2.16 mol) of maleic acid anhydride were melted at 50° C., to which were added dropwise 417 g (2.40 mol) of 2-trimethoxy)-silyl-1,3-butadiene [II]slowly while maintaining the reaction temperature at 50°-60° C. After the dropping was completed, stirring was continued for further one hour.

Then, the reaction product was fractionated to obtain 468 g (1.72 mol) of clear colorless liquid 4-(trimethoxy)silyl-1,2,3,6-tetrahydrophthalic acid anhydride [I](yield: 80 %, purity: 99%, Boiling point: 160°-163° C./1 mmHg).

EXAMPLE 5

2.0 g (0.02 mol) of maleic acid anhydride were dissolved into 5 ml of benzene at 50° C., to which were added dropwise 3.5 g (0.014 mol) of 2-(triisoprpoxy)-silyl-1,3-butadiene [II]slowly maintaining the reaction temperature at 50°-60° C. After the dropping was completed, stirring was continued for further one hour.

After removing benzene and unreacted 2-(triisopropoxy)silyl-1,3-butadiene by distilation under a reduced pressure, the residue was subjected to bulb to bulb distillation to obtain clear colorless liquid 4-(triisopropoxy)silyl-1,2,3,6-tetrahydrophthalic acid anhydride [I](yield: 50 %, purity: 97 %, boiling point: 150° C./0.2 mmHg).

HNMR (CDCl$_3$): (Internal standard: tetramethylsilane) $\delta$1.14 (d, 18H, J=7Hz), 2.10-2.85 (m, 4H), 3.25-5.40 (m, 2H), 4.19 (Hepted, 3H, J=7Hz)

IR (neat): 2955, 1840, 1775, 1480, 1468, 1035, 933 cm$^{-1}$

MASS: 356 (21, M+), 341 (88), 298 (65), 297 (98), 283 (100), 79 (97)

EXAMPLE 6

2.0 g (0.02 mol) of maleic acid anhydride were dissolved into 5 ml of benzene at 50° C., to which were added dropwise 3.5 g (0.022 mol) of 2-(dimethoxymethyl)-silyl-1,3-butadiene [II]slowly while maintaining the reaction temperature at 50°-60° C. After the dropping was completed, stirring was continued for further one hour.

After removing benzene and unreacted 2-(dimethoxymethyl)silyl-1,3-butadiene under a reduced pressure, the residue was subjected to bulb to bulb distillation to obtain clear colorless liquid 4-(dimethyoxymethyl)silyl-1,2,3,6-tetrahydrophthalic acid anhydride [I](yield: 55 %, purity: 91 %, boiling point: 130° C./0.2 mmHg).

HNMR (CDCl$_3$): (Internal standard: tetramethylsilane) $\delta$0.16 (S, 3H), 2.08-2.92 (m, 4H), 3.3-3.5 (m, 2H), 3.48 (S, 3H), 3.49 (S, 3H), 6.42-6.66 (m, 1H)

MASS: 241 (100, M+ −15), 183 (13), 169 (52), 143 (34), 105 (85), 91 (28), 75 (13)

REFERENCE EXAMPLE 1

To a mixed solution of 15 ml (0.153 mol) of 1,4-dichloro-1-butyne [IV]and 13.6 ml (0.16 mol) of trichlorosilane (bp: 31°-32° C.) [V], were added 0.15 ml (10 mmol) of H$_2$PtCl$_6$·6H$_2$O in an isopropyl alcohol solution (0.05 g/ml), which were heated for 8 hours. Then, it was directly distillated to obtain 37 g of 1,4-dichloro-2-(trichloro)silyl-2-butene [VI](yield: 94 %, bp: 70° C./1 mmHg).

Then, a mixture of 6.9 g (82×1.3 mmol) of Zn powder and 20 ml of THF was cooled to −15° C., to which was slowly added, under sufficient stirring, a mixed solution of 21.3 g (82 mmol) of 1,4-dichloro-2-(trichloro)silyl-2-butene [VI]and 10 ml of THF. Then, stirring was effected at −15° C. for one hour and 60 ml of dry pentane were added. After filtering the deposited ZnCl$_2$ and removing the solvent through the distillation under a reduced pressure at low temperature (−20° C.), 13 g of 2-(trichloro)silyl-1,3-butadiene [II-d]were obtained (yield: 85 %).

Further, a mixed solution of 8.7 g of the 2-(trichloro)silyl-1,3-butadiene [II-d](46 mmol) of crude product) and 10 ml of THF was cooled to −10° C. and, while stirring sufficiently, a mixed solution of 8.3 ml (46×3×1.5 mmol) of CH$_3$OH and 28.9 ml (46×3×1.5 mmol) of (C$_2$H$_5$)$_3$N were slowly added dropwise. Then, the solution was stirred at room temperature for 30 minutes and 30 ml of (C$_2$H$_5$)$_2$O were added. The deposited (C$_2$H$_5$)$_5$N·HCl was filtered out and the solvent was distilled off under a reduced pressure and 6.1 g of 2-(trimethoxy)silyl-1,3-butadiene [II-a]were obtained through the distillation under a reduced pressure (yield: 75 %).

REFERENCE EXAMPLE 2

A solution of 14.2 g (55 mmol) of 1,4-dichloro-2-(trichloro)silyl-2-butene [VI]in 7 ml of THF was cooled to −10° C., to which was slowly added dropwise a mixed solution of 10 ml of CH$_3$OH (55×3×1.5 mmol) and 34.5 ml of (C$_2$H$_5$)$_3$N (55 x 3 x 1.5 mmol). Then, it was stirred at room temperature for one hour and 30 ml of dry ether were added. After filtering out the (C$_2$H$_5$)$_3$N·HCl and removing the solvent through distillation under a reduced pressure, 10.8 g of 1,4-dichloro-2-(trimethoxy)silyl-2-butene [VII](yield: 80 %, bp: 88°-90° C./1-2 mmHg).

Then, while stirring 4.0 g (41×1.5 mmol) of Zn powder and 15 ml of THF sufficiently, 10 g (41 mmol) of 1,4-dichloro-2-(trimethoxy)silyl-2-butene [VII]prepared by the method as described above were added. After heating the mixed solution under reflux for one hour, it was cooled to room temperature and 30 ml of dry pentane were added for deposition. After filtering out the deposited ZnCl₂ and removing the solvent through distillation under a reduced pressure, 5.0 g of 2-(trimethyoxy)silyl-1,3-butadiene [II-a]were obtained through the distillation under a reduced pressure (yield): 70 %, boiling point: 24° C./1 mmHg).

REFERENCE EXAMPLE 3

To 120 ml (0.7 mol) of 1,4-dichloro-2-(trichloro-silyl-2-butene [VI]was slowly added dropwise 160 ml of dehydrated isopropyl alcohol at room temperature, followed more 80 ml of dehydrated isopropyl alcohol was added. Hydrogenchloride was generated during the dropping, thereafter, the mixture was stirred at room temperature for 20 minutes. The remaining hydrogenchloride was removed at room temperature under a reduced pressure and the solvent distilled off at 40° C./1–5 mmHg.

Then, while stirring 55 g of Zn powder, 6 g of ZnCl₂ and 100 ml of THF sufficiently, the residue was slowly added dropwise at 45°–65° C.

After the reaction, reaction mixture was cooled to room temperature and 200 ml of dry n-hehane were added for deposition.

After filtering out the deposited ZnCl₂ and removing the solvent through distillation under a reduced pressure, 80 g (0.32 mol) of 2-(triisopropoxy)silyl-1,3-butadiene [II]were obtained through the distillation (yield: 46 % based on 1,4-dichloro-2-(trichloro)-silyl-2-butene, purity: 90 %, boiling point: 70° C./0.5 mmHg).

REFERENCE EXAMPLE 4

To a mixture of 10 ml (0.0106 mol) of 1,4-dichloro-2-butyne [IV]and 11.5 ml (0.11 mol) of dichloromethylsilane (boiling point: 41° C.) was added 0.05 ml (4.8 mmol %) of an isopropanol solution of chloroplatinic acid prepared following by heating under reflux for 1 hour, thereafter, the mixture was directly distilled to obtain 2-(dichloromethyl)silyl-2-butene (yield: 87 %, boiling point: 57° C./1 mmHg).

11.5 g (48 mmol) of 1,4-dichloro-2-(dichloromethyl)-silyl-2-butene, 1.0 l of THF, 5.9 ml (4.8× 2×1.5 mmol) of (C₂H₅)₃N, and 30 ml of (C₂H₅)₂O were used and subjected to vacuum distillation, thereby obtaining 8.8 g of 1,4-dichloro-2-(dimethoxymethyl)-silyl-2-butene [VII]. (yield: 80 %, boiling point: 63° C./1 mmHg).

While 3.5 g (35×1.5 mmol) of Zn powder and 15 ml of THF were agitated, 8.0 g (35 mmol) of 1,4-dichloro-2-(dimethoxymethyl)silyl-2-butene was added. The mixture was heated under reflux for 2 hours, and then treated in the same manner as in Example 1 to obtain 3.9 g of 1,4-dichloro-2-(dimethoxymethyl)silyl-l2-butadiene II. (yield: 71 %, boiling point: 31° C./10–12 mmHg).

What is claimed is:

1. A 4-substituted-1,2,3,6-tetrahydrophthalic acid anhydride compound represented by the structural formula:

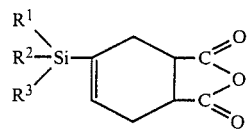

wherein $R^1$ and $R_2$ each represents a lower alkoxy group, and $R^3$ represents a lower alkoxy group or a lower alkyl group, said 4-substituted-1,2,3,6-tetrahydrophthalic acid anhydride being a liquid.

2. The 4-substituted-1,2,3,6-tetrahydrophthalic acid anhydride as defined in claim 1, wherein the compound is 4-(diloweralkoxy methyl)silyl-1,2,3,6,-tetrahydrophthalic acid anhydride represented by the formula:

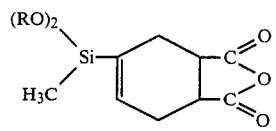

wherein R represents a lower alkyl group.

3. The 4-substituted-1,2,3,6-tetrahydrophthalic acid anhydride as defined in claim 1, wherein the compound is 4-(dimethyoxy methyl)silyl-1,2,3,6-tetrahydrophthalic acid anhydride.

4. The 4-substituted-1,2,3,6-tetrahydrophthalic acid anhydride as defined in claim 1, wherein the compound is 4-trimethoxy)silyl-1,2,3,6-tetrahydrophthalic acid anhydride.

5. The 4-substituted-1,2,3,6-tetrahydrophthalic acid anyhydride as defined in claim 1, wherein the compound is 4-(triethoxy)silyl-1,2,3,6-tetrahydrophthalic acid anhydride.

6. The 4-substituted-1,2,3,6-tetrahydrophthalic acid anhydride as defined in claim 1, wherein the compound is 4-(tripropoxy)silyl-1,2,3,6-tetrahydrophthalic acid anhydride.

7. The 4-substituted-1,2,3,6-tetrahydrophthalic acid anhydride as defined in claim 1, wherein the compound is 4-(triloweralkoxy)silyl-1,2,3,6-tetrahydrophthalic acid anhydride represented by the structural formula:

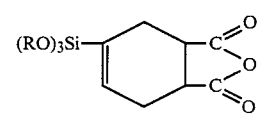

wherein R represents a lower alkyl group.

8. The 4-substituted-1,2,3,6-tetrahydrophthalic acid anhydride as defined in claim 1, wherein the compound is 4-(diloweralkoxy loweralkyl)silyl-1,2,3,6-tetrahydrophthalic acid anhydride represented by the structural formula:

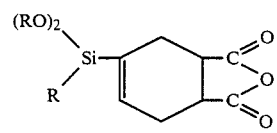

where R represents a lower alkyl group.

* * * * *